United States Patent [19]

Gomes de Matos et al.

[11] Patent Number: 5,210,329
[45] Date of Patent: May 11, 1993

[54] PROCESS FOR PREPARING BISPHENOL-A

[75] Inventors: Isabel M. Gomes de Matos, Evansville, Ind.; Allen Wai-Kee Ko, Brasschaat, Belgium

[73] Assignee: General Electric Company, Pittsfield, Mass.

[21] Appl. No.: 836,483

[22] Filed: Feb. 18, 1992

[51] Int. Cl.$^5$ .................... C07C 37/20; C07C 37/68; C07C 39/16

[52] U.S. Cl. .................... 568/727; 568/722; 568/723; 568/724

[58] Field of Search ............ 568/722, 724, 727, 728, 568/723, 749

[56] References Cited

U.S. PATENT DOCUMENTS

| | | | |
|---|---|---|---|
| 3,627,846 | 12/1971 | Meyer | 568/724 |
| 4,529,823 | 7/1985 | Mendiratta | 568/724 |
| 4,942,265 | 7/1990 | Iimuro et al. | 568/724 |
| 5,105,026 | 4/1992 | Powell et al. | 568/727 |

Primary Examiner—Werren B. Lone

[57] ABSTRACT

A process which comprises reacting phenol and acetone in the presence of an acidic catalyst and thereafter a. isolating first major portion of bisphenol-A, therefore forming a purge stream comprising bisphenol-A, bisphenol-A isomers and tar,
b. adding or taking from the said purge stream, if necessary, sufficient phenol so as to bring the purge stream ratio of phenol to bisphenol-A to about 5:1 to 15:1 based on moles, thereby forming an altered purge stream,
c. bringing the temperature of the altered stream to a range of about 30°-50° C.,
d. maintaining the temperature of the altered stream at about 30°-50° C. until about 60-85% of the bisphenol-A crystallizes as a bisphenol-A/phenol 1:1 molar adduct,
e. separating the adduct from its mother liquor.

7 Claims, No Drawings

PROCESS FOR PREPARING BISPHENOL-A

BACKGROUND OF THE INVENTION

Bisphenol-A is prepared commercially by reaction of phenol and acetone in contact with an acidic catalyst such as hydrochloric acid or an acidic ion exchange resin such as a sulfonic acid substituted polystyrene. As would be expected, the reaction is not 100% directed to the formation of bisphenol-A. A significant number and quantity of undesirable by-products, some of which are highly colored are also formed. These undesirable by-products affect bisphenol-A yield and quality. They are particularly significant when bisphenol-A is converted into polycarbonate. A high degree of purity of bisphenol-A with respect to wt. % impurities and color of the bisphenol-A is therefore required for preparation of quality polycarbonate.

In preparing the bisphenol-A, the acetone is contacted with a substantial excess of phenol, usually 6 times or more the stoichiometric amount necessary while in the presence of the acidic catalyst. The initial separation of bisphenol-A from excess phenol and by-products from the reactor effluent is usually carried out by distillation separation of phenol and bisphenol or phenol bisphenol-A adduct crystallization.

In this manner, the major portion of the bisphenol-A is removed from the by-products and impurities. There are a number of methods for handling the impurities by-products rich stream after removal of the major portion of the bisphenol-A. For example, such a stream can be (a) partially recycled to the condensation reactor, (b) fed to an "isomerization" reactor to convert various bisphenol-A geometric isomers and related compounds to bisphenol-A, (c) excess phenol removed, (d) burned, (e) distill off further bisphenol-A and the like. Generally when bisphenol-A is recovered from these streams the recovery method is distillation.

We have discovered a new, feasible and economic system to recover bisphenol-A from streams, usually referred to as purge streams, which remain after the first major portion of bisphenol-A has been removed, usually by distillation or phenol/bisphenol-A adduct formation. This purge stream is comprised of bisphenol-A, zero to small or even large quantities of phenol depending on whether excess phenol is partially or completely removed prior to the first major isolation of bisphenol-A or thereafter, and the remainder of the stream comprised of bisphenol isomers and somewhat higher molecular weight and related compounds, generally referred to as tar. This new method is advantageous compared to a distillation method because it has lower investment costs, lower operating costs, lower operating temperature. The process provides a product with improved quality.

SUMMARY OF THE INVENTION

In accordance with the invention there is a process which comprises a. isolating first major portion of bisphenol-A, therefore forming a purge stream comprising bisphenol-A, bisphenol-A isomers and tar, b. adding or taking from the said purge stream, if necessary, sufficient phenol so as to bring the purge stream ratio of phenol to bisphenol-A to about 5:1 to 15:1 based on moles, thereby forming an altered purge stream, c. bringing the temperature of the altered stream to a range of about 30°–50° C., d. maintaining the temperature of the altered stream at about 30°–50° C. until about 60–85% of the bisphenol-A crystallizes as a bisphenol-A/phenol 1:1 molar adduct, e. separating the adduct from its mother liquor.

Further aspects of the invention include separating the bisphenol-A from the adduct and, if desired, converting the bisphenol-A to a polymer, for example polyepoxides and polyetherimide but particularly polycarbonate if further standard purification steps of the bisphenol-A are employed. Standard processes can be used to convert the bisphenol-A to polycarbonate, for example interfacially using the alkali metal salt of bisphenol-A in contact with an organic solvent such as methylene chloride, and a carbonate precursor such as phosgene with an amine catalyst such as triethylamine. Melt polymerization utilizing bisphenol-A and diphenylcarbonate or a differing carbonate precursor under heat and an alkaline catalyst can also be employed.

The mother liquor portion of step d, containing the impurities and some bisphenol-A can be treated in various manners but it is preferably at least partially recycled to the equipment in which the adduct crystallization, usually referred to as a "crystallizer", occurs so as to remove further bisphenol-A and provide an even more purified bisphenol-A.

Still further another aspect of the invention includes the addition of water into the bisphenol-A crystallizer (1) together with the altered stream or (2) at the time crystallization of the bisphenol-A adduct begins to occur. This water seems to perform as a habit modifier resulting in better filterability of the adduct and therefore better quality. It also appears to act as a "cleanser", thereby keeping the crystallizer and crystallizer heat exchanger surfaces free of deposits for longer periods of time. The water is introduced at a level of about 0.5–5 wt. % of the weight of the altered stream.

DETAILED DESCRIPTION OF THE INVENTION

Bisphenol-A is made by the standard method of contacting a stoichiometric excess of phenol with acetone over an acidic catalyst. All or essentially all the acetone is converted into products as aforestated. The condensation reaction is carried out at an elevated temperature, for example from about 54.4° C. to 85° C. The bisphenol-A is recovered after the condensation reaction by distillation and/or crystallization. Generally, if bisphenol-A is initially recovered by distillation, a substantial portion of the phenol is distilled off before since the phenol is lower boiling than the bisphenol-A. Therefore the bottom or purge stream of the bisphenol-A has very little phenol but is rich in bisphenol-A, its geometric isomers such as 2,4' bisphenol-A and related somewhat heavier compounds referred to as tar. Another recovery method for the bisphenol-A is to form a bisphenol-A/phenol crystalline adduct. Approximately 50 to 70 wt. % of the bisphenol-A in the reactor effluent is recovered in this manner. The purge stream, that is mother liquor in this case is rich in phenol as well as bisphenol-A impurities since there usually is no prior removal of phenol.

The value of bisphenol-A in these streams has been recovered, when desired, by distillation. The new method, phenol/bisphenol-A adduct crystallization, allows the recovery to be more economically performed because of lower investment and operating costs compared to distillation.

The phenol content of the purge stream containing bisphenol-A is altered by adding or removing phenol, as the case may be, to bring the molar ratio of phenol to bisphenol-A to about 5:1 to 15:1, preferably 7.0 to 10.0:1. The temperature of this altered stream is then lowered, if necessary, to about 30°–50° C. preferably 39°–45° C. Generally at least part of this cooling step takes place in a special piece of recovery equipment called a crystallizer, for example an externally cooled magna crystallizer. This equipment is particualarly designed to facilitate a fast and uniform crystallization. At this temperature the adduct of bisphenol-A/phenol crystallizes and is collected. The mother liquor containing the isomeric by-products and other materials as well as some bisphenol-A is removed and treated in a further manner by partially recycling to the crystallizer for further bisphenol-A recovery, preferable, or distilled, burned or treated in a further manner. The recovered phenol/bisphenol-A adduct is then washed with phenol, if an even purer product is desired. The phenol can then be removed from the adduct by standard methods such as melting followed by distillation and the like or such aduct can then be recycled back to the main process. The bisphenol-A is converted into solid form and then used for preparing polymers such as polymeric epoxides. Where particularly high quality bisphenol-A is needed, as in polycarbonate, the adduct can be recycled to the reactor effluent for further purification procedures. Bisphenol-A is then recovered. Polycarbonate is prepared by any of the standard methods such as interfacially reacting bisphenol-A in caustic solution at an alkaline pH with phosgene in methylene chloride using an amine catalyst or in the melt - for example reacting bisphenol-A with diphenyl carbonate at elevated temperature with an alkaline catalyst such as sodium hydroxide or a metal.

The following are examples of the invention. These examples are intended to illustrate the broad inventive concept disclosed in this patent application.

EXAMPLE 1

Bisphenol-A was made and purified under standard conditions. The mother liquor stream was passed through an isomerization reactor followed by distillation to remove phenol as overhead. The bottoms, purge stream, was then removed and to it was added enough phenol to have a 4:1 weight ratio of phenol to bisphenol-A. This altered purge stream was maintained at a temperature of 74° C. This stream was then pumped to a crystallizer, cooled to 42° C. and bisphenol-A/phenol adduct crystallized. The adduct was separated from the mother liquor, heated to separate therefrom the phenol which was subsequently distilled.

The bisphenol-A had an absorbance at 350 Nm of 0.89, a purity of 87.8% and a yield of 78% based on pp/BPA.

What is claimed is:

1. A process which comprises reacting phenol and acetone in the presence of an hydrochloric or ion exchange acidic catalyst and thereafter
   a. isolating first major portion of bisphenol-A, therefore forming a purge stream comprising bisphenol-A, bisphenol-A isomers and tar,
   b. adding or taking from the said purge stream, if necessary, sufficient phenol so as to bring the purge stream ratio of phenol to bisphenol-A to about 5:1 to 15:1 based on moles, thereby forming an altered purge stream,
   c. bringing the temperature of the altered stream to a range of about 30°–50° C.,
   d. maintaining the temperature of the altered stream at about 30°–50° C. until about 60–85% of the bisphenol-A crystallizes as a bisphenol-A/phenol 1:1 molar adduct,
   e. separating the adduct from its mother liquor.

2. The process in accordance with claim 1 wherein phenol is also present in the purge stream.

3. The process in accordance with claim 1 wherein bisphenol-A is from about 50–75 wt. % of the purge stream.

4. The process in accordance with claim 1 wherein the temperature in step c is from about 39°–46° C.

5. The process in accordance with claim 1 wherein water is added to the purge stream prior to initiation of the crystallization of adduct in step d.

6. The process in accordance with claim 5 wherein the water is from about 0.5–5.0 wt. % of the purge stream immediately prior to crystallization.

7. A process in accordance with claim 1 wherein in step a there is essentially no phenol.

* * * * *